US007018625B2

(12) United States Patent
Ulmer et al.

(10) Patent No.: US 7,018,625 B2
(45) Date of Patent: *Mar. 28, 2006

(54) PERSONAL CARE COMPOSITIONS

(75) Inventors: Herbert Ulmer, Bussum (NL); Timothy Gillece, Pompton Plains, NJ (US); John Katirgis, West Caldwell, NJ (US)

(73) Assignee: ISP Investments Inc., Wilmington, DE (US)

( * ) Notice: Subject to any disclaimer, the term of this patent is extended or adjusted under 35 U.S.C. 154(b) by 114 days.

This patent is subject to a terminal disclaimer.

(21) Appl. No.: 10/722,787

(22) Filed: Nov. 26, 2003

(65) Prior Publication Data

US 2004/0166081 A1     Aug. 26, 2004

Related U.S. Application Data

(60) Provisional application No. 60/449,248, filed on Feb. 20, 2003.

(51) Int. Cl.
*A61K 31/785* (2006.01)
*A61K 31/797* (2006.01)
*A61K 31/77* (2006.01)
*A61K 31/765* (2006.01)
*A61K 31/80* (2006.01)

(52) U.S. Cl. .............................. 424/78.36; 424/78.32; 424/78.33; 424/78.37; 424/78.38

(58) Field of Classification Search ............... 424/400, 424/70.17, 78.38
See application file for complete search history.

(56) References Cited

U.S. PATENT DOCUMENTS 5,994,385 A * 11/1999 Ulmer et al. ............... 514/397
6,025,501 A * 2/2000 Ulmer et al. ............... 548/545
2004/0042989 A1* 3/2004 Ulmer et al. ............ 424/70.11

OTHER PUBLICATIONS

Hutsman Technical Bulletin, The Jeffamine Polyoxyalkylene Amines, 1987, pp. 1-6.*

* cited by examiner

*Primary Examiner*—Thurman K. Page
*Assistant Examiner*—David Vanik
(74) *Attorney, Agent, or Firm*—Walter Katz; William J. Davis

(57) ABSTRACT

Personal care compositions, particularly hair care products, include a polymer mixture made from (A) a derivatized polymer of maleic anhydride having defined repeat units of a monomer (e.g. α-olefin) maleic anhydride alkyl half-ester or full acid, maleamic acid and maleimide, and (B) a compound or polymer having a carboxylic acid functionality. These compositions exhibit excellent high humidity curl retention properties, as well as an advantageous blend of toughness and cohesiveness, and a strong affinity to natural fibers such as keratin-based fibers, e.g. hair, skin, or textiles, such as cotton or wool; and they are also water-soluble and water-resistant.

17 Claims, 1 Drawing Sheet

FIGURE
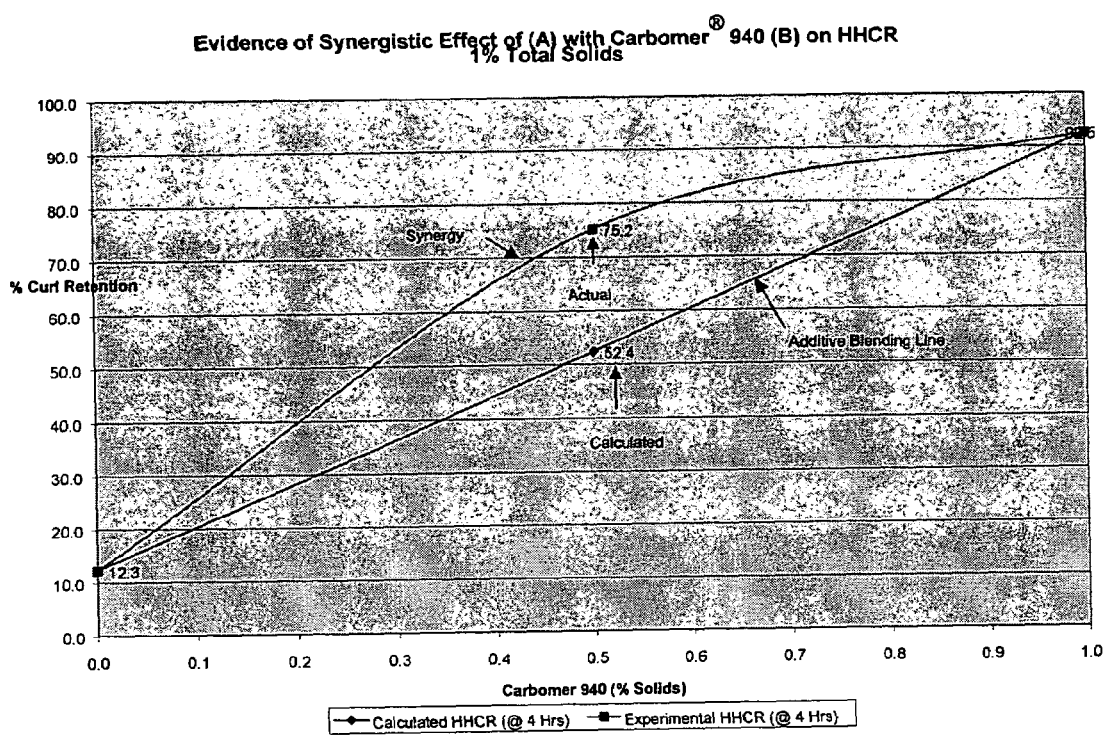

PERSONAL CARE COMPOSITIONS

CROSS-REFERENCE TO RELATED U.S. PATENTS

This application is based upon provisional application Ser. No. 60/449,248, filed Feb. 20, 2003 and U.S. Ser. No. 10/353,390, filed Jan. 29, 2003, which is a continuation-in-part of U.S. Ser. No. 10/233,838, filed Aug. 30, 2002, and assigned to the same assignee, and related to U.S. Pat. Nos. 5,869,695; 5,886,194; 5,959,122; 5,994,385; and 6,025,501, also assigned to the same assignee as herein.

BACKGROUND OF THE INVENTION

1. Field of the Invention

This invention relates to personal care compositions, and, particularly, to such compositions containing a mix of hair styling polymers and a compound or polymer having a carboxylic acid functionality, which impart the desirable physical attributes of toughness and cohesiveness, and a smooth feel, as well as high humidity curl retention, water-solubility and water-resistance.

2. Description of the Prior Art

Hair styling polymers which feel stiff on hair are typically rather brittle under a high applied stress; accordingly, these polymers shatter easily when strained appreciably. On the other hand, highly flexible polymers will bend under both high and low stress but they are generally considered by the user to be too soft for desirable hair styling.

In the aforementioned co-pending patent applications, and patents, polymers are described which have the desirable attributes of stiffness and flexibility, and have a strong affinity for hair, imparting a natural feel for the user, and are also water-soluble and water-resistant. These natural feel polymers can be easily removed from a substrate such as hair or skin, or a textile fiber, by simple washing.

Accordingly, it is an object of this invention to provide improved personal care compositions containing polymers which exhibit toughness and cohesiveness.

Another object is to provide hair care compositions made by mixing such polymers with a compound or polymer having a carboxylic acid functionality, which gives the blend the desired properties of excellent high humidity curl retention properties, water solubility and water-resistance.

These and other objects and features of the invention will be made apparent from the following description thereof.

IN THE DRAWINGS

The FIGURE is a graphical representation of % Curl Retention vs % Carbomer® in compositions of the invention showing synergistic effect of components thereof.

SUMMARY OF THE INVENTION

The personal care compositions include polymers made by mixing (A), which are polymers having defined amounts of repeat units of (a) a monomer (e.g. α-olefin)-maleic anhydride alkyl half-ester or full acid, (b) maleamic acid, and (c) a maleimide, as shown below:

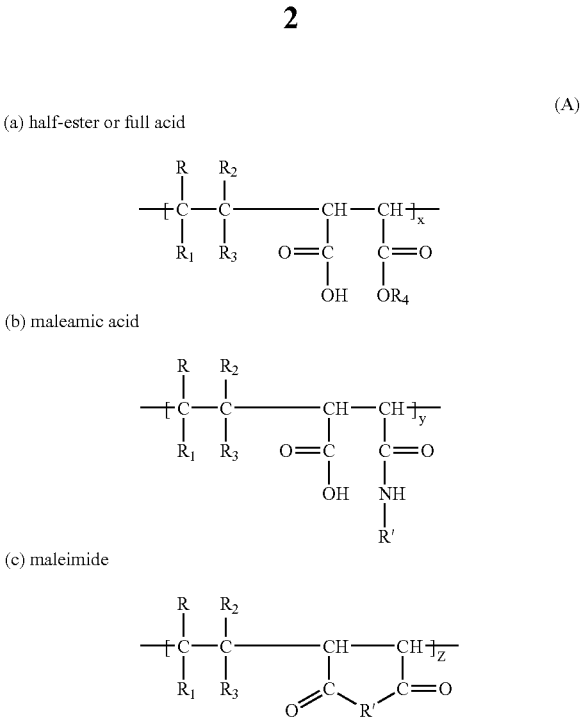

where:

R, $R_1$, $R_2$ and $R_3$ are selected from H, alkyl, alkoxy, cycloalkyl, aryl, ester, acid, hydroxy, hydroxyalkyl, amido, amino, lactam, chloro, fluoro, halo and silyl, and $R_4$ is H or alkyl; and R' is a derivatizing group selected from X, a hydrophobic amine; Y, a hydrophilic amine; and Z, a polyether amine; and suitable mixtures thereof;

x, y and z are present, in mole %, of 0–99.9, 0–50 and 0.1–100, respectively; preferably 0–50, 0–5 and 50–100; and X, Y and Z preferably are present in mole ratios of 0–50:0–100:0–20; most preferably, 0–10:40–98:1–10; and (B) a compound or polymer with a carboxylic acid functionality.

Typical hair care compositions herein are used in the modes of styling, mousse, gel and spray hair care products. These compositions performed well in practice giving the user the advantages of the natural feel polymers therein, particularly a firm and flexible characteristic, water-resistance and water-solubility, and excellent high humidity curl retention, and predetermined viscosity.

DETAILED DESCRIPTION OF THE INVENTION

The (A) polymer component of the polymers used in personal care compositions herein is particularly characterized by repeat units which contain an abundance (by weight) of an amine derivatizing group which can hydrogen-bond or ionically-bond with itself or other repeat units in the polymer forming intra- or inter-molecular bonds in the polymer. This results in a pseudo-network polymer. Cohesion between such hydrogen-bonded or ionically-bonded molecules provides the polymer with water-resistance, but also with water solubility because, once the polymer is flooded with water, it will admit sufficient amount of water for solubilization. These polymers show good adhesion to natural substrates but can be removed easily if desired. Some amine derivatizers may also crystallize upon dry-down, resulting in enhanced water resistance and physical properties.

Representative structural components of the (A) polymers of the invention are given below.

Polymer Backbone

Monomer-Maleic Anhydride Copolymer

Alkyl vinyl ether-maleic anhydride copolymer, e.g. methyl vinyl ether-maleic anhydride copolymer, or isobutyl vinyl ether-maleic anhydride copolymer, etc., alpha-olefin-maleic anhydride copolymer, e.g. ethylene-maleic anhydride copolymer, or isobutylene-maleic anhydride copolymer; styrene-maleic anhydride copolymer, etc., acrylate-maleic anhydride copolymer, e.g. acrylic acid-maleic anhydride copolymer, methyl methacrylate-maleic anhydride copolymer, etc., vinyl-maleic anhydride copolymer, e.g. vinyl chloride-maleic anhydride copolymer, vinyl pyrrolidone-maleic anhydride copolymer, etc., diene-maleic anhydride copolymer, e.g., butadiene-maleic anhydride copolymer, and derivatives thereof, and the like.

Derivatizers

Hydrophobic Amine (X)

Monofunctional α-unsubstituted primary or secondary monoamines, unsubstituted or substituted with alkyl, aryl, heterocyclic, aromatic, fluoro, silyl amino, carboxy and halogen; e.g. $C_1$–$C_{40}$ alkyl $NH_2$; butylamine, isobutyl amine, and octadecylamine. These amines may be included in the polymer to alter the solubility of the polymer.

Hydrophilic Amine (Y)

Hydroxy α-unsubstituted amines e.g. ethanolamine, isopropylamine, isopropanolamine, 3-amino-1-propanol; methoxyethyl amine, and diglycol amine; and alkyl diamines, e.g. 3-(dimethylamino)propylamine, N,N-dimethylethylenediamine, N-aminopropyl pyrrolidone, N-aminoethyl pyrrolidone, 1-(3-aminopropyl)imidazole and silicone amines. These amines are included in the polymer to modify the adhesive/cohesive balance in the polymer, and to increase compatibility with other components in system.

Polyether Amine (Z)

Polyoxyalkylene amine, having the formula:

$$R_5\!-\!\!(\!O\!-\!CH_2\!-\!CH\!)_n\!\!-\!(\!O\!-\!CH_2\!-\!CH\!)_m\!-\!NH_2$$
$$\phantom{R_5\!-\!\!(\!O\!-\!CH_2\!-\!}R^6 \phantom{\!)_n\!\!-\!(\!O\!-\!CH_2\!-}CH_3$$

where $R_5$ and $R_6$ are selected from H and alkyl; e.g. $R_5$ is $CH_3$ and $R_6$ is H; and $R_5$ is $CH_3$ and $R_6$ is $CH_3$; and n and m are integers from 1–50; e.g. n=32 and m=10. These amines are obtainable as Jeffamine® M Monoamines (Huntsman Corp), with various molecular weights and ethylene oxide (EO)/propylene oxide (PO) ratios. These amines are present to provide natural feel properties in the polymer, i.e. softness and flexibility, as well as adhesive/cohesive balance and to modify solubility.

The personal care compositions herein are made by mixing (A) with (B), a compound or polymer having a carboxylic acid functionality. Carboxylic acid functionality includes the free acid and the neutralized acid. A particularly preferred (B) polymer is a linear or crosslinked acrylic acid polymer, e.g. Carbopol®, preferably which is neutralized before mixing with (A). The result of mixing (A) and (B) is a complexed, synergistic product particularly suitable for hair care application because it has high humidity curl retention, and may have an increased solution viscosity, as compared to (A) or (B) alone. The viscosity of the product can be predetermined by the relative amounts of (a), (b) and (c) in polymer (A). For example, 100 mole % in the (c) repeat unit will provide an opaque, more viscous, product, while dilution of the polymer with more (a) repeat units will form a more desirable clear, and less viscous product, upon mixing with (B).

The polymers strongly interact and upon dry down result in films with increased toughness and cohesiveness than individual polymer systems.

When these synergistic systems are used in a personal care hair styling application the resultant formulations have improved high humidity and curl retention (HHCR) when compared to similar formulations containing the individual polymers alone.

The degree of complexation between (A) and (B) can be predetermined by adjusting the mole ratio of maleimide in (A) to the carboxylic units in (B). Complexation is strongest for products in which the maleimide:carboxylic mole ratio approaches 1:1.

However, complexation is not as pH sensitive as typical acid-base complexed systems, e.g. PVP and acrylic acid; in fact, complexation can occur at a neutral pH. Thus personal care formulations at or around a neutral pH still possess synergistic complexation complexation of (A) and (B), with its resultant desirable properties and physical attributes.

Referring to the FIGURE, there is shown a dramatic increase in HHCR which is evident for the 50:50 blend of (A) with Carbomer® 940 (B). The actual experimental value of 75.2% curl retention after 4 hours is much higher than the calculated value of 52.4% which is expected if the interaction of the two polymers had merely an additive effect.

The invention will now be described with reference to the following examples.

EXAMPLE 1

Step 1

Preparation of Polymer (A)

The following were charged into a 2-liter, stainless steel high pressure reactor.

| | |
|---|---|
| P(maleic anhydride/isobutene) (Man) | 72.94 g |
| 3-(dimethylamino) propylamine (50 mol % based on Man) | 24.17 g |
| Jeffamine ® M-2070 (2 mol % based on Man) (M.W. 2,000, 70/30 EO/PO) (water soluble) | 20.73 g |
| Triethylamine (43 mol % based on Man) (Neutralizer) | 20.59 g |
| Methanol | 257.07 g |

The reactor was sealed, purged 3 times with $N_2$ gas, and heating was begun according to the following heating profile.

| | |
|---|---|
| Ambient → | 90° C., 1½ hr. |
| 90° C. → | 90° C., 2 hr. |
| 90° C. → | 130° C., 1½ hr. |
| 130° C. → | 130° C., 8 hr. |
| 130° C. → | 35° C., 1 hr. |

At the end of the heating cycle, the polymer product was obtained as a lightly viscous, yellow, clear solution; then it was flooded with water to give a viscous, hazy, yellow-colored solution.

Step 2

Mixing Polymer (A) with Carboxylic Acid Containing Polymer (B)

The polymer solution (A) was mixed with neutralized Carbopol®, a crosslinked acrylic acid polymer, in amounts of 2 and 0.5 wt. %, respectively, and in an amount present in a typical styling gel formulation. A thick gel having a viscosity greater than (A) or (B) was obtained after an hour. The gel formulation was applied to hair and the resultant film was stressed. The film showed a natural feel, combining firm and flexible characteristics, water-resistance and water-solubility, and excellent high humidity curl retention.

EXAMPLE 2

Step 1

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 42.35 g |
| (M.W. 2,000, 5/95 EO/PO (water-insoluble)) | |
| Jeffamine M-2070 | 42.35 g |
| (M.W. 2,000, 70/30 EO/PO (water-soluble)) | |
| Triethylamine | 31.30 g |
| Ethanol | 510.20 g |

The reactor was sealed and purged with an inert gas. The following heating profile was initiated:

| | |
|---|---|
| Heat to 125° C. | 4 hours |
| Hold at 125° C. | 12 hours |
| Cool to 35° C. | 1 hour |

After the heating profile was complete, the polymer solution was discharged from the reactor. The resultant material was a viscous, clear yellow solution. This material was laid down as a film and allowed to dry. A non-brittle film resulted which was water soluble. Exchanging ethanol for water gave a water-based polymer solution having similar properties to the ethanol-based material.

Step 2

This step was carried out as in Example 1 to provide similar results.

EXAMPLE 3

Step 1

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 84.70 g |
| Triethylamine | 31.30 g |
| Ethanol | 510.20 g |

The reactor was sealed and purged with an inert gas. The following heating profile was initiated:

| | |
|---|---|
| Heat to 125° C. | 4 hours |
| Hold at 125° C. | 12 hours |
| Cool to 35° C. | 1 hour |

After the heating profile was complete, the polymer solution was discharged from the reactor. The resultant product was a viscous, clear yellow solution. This material was laid down as a film and allowed to dry. A non-brittle film resulted. Exchanging with water gave a water-based polymer solution having similar properties to the ethanol-based material.

Step 2

This step was carried out as in Example 1 to provide similar results.

EXAMPLE 4

Step 1

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 84.70 g |
| Jeffamine M-2070 | 33.90 g |
| Triethylamine | 31.30 g |
| Ethanol | 573.17 g |

The reactor was sealed and purged with an inert gas. The following heating profile was initiated:

| | |
|---|---|
| Heat to 125° C. | 4 hours |
| Hold at 125° C. | 12 hours |
| Cool to 35° C. | 1 hour |

After the heating profile was complete, the polymer solution was discharged from the reactor. The resultant material was a viscous clear yellow solution. This material, when laid down as a film and allowed to dry, resulted in a flexible film. This same material can be exchanged with water to give a water-based polymer solution having similar properties to the ethanol-based material.

Step 2

This step was carried out as in Example 1 to provide similar results.

EXAMPLE 5

Step 1

The following reactants were added to a 2-liter pressure reactor:

| | |
|---|---|
| Poly(isobutylene/maleic anhydride) | 119.22 g |
| Dimethylaminopropylamine | 39.51 g |
| Jeffamine M-2005 | 101.70 g |
| Jeffamine M-2070 | 84.70 g |
| Triethylamine | 31.30 g |
| Ethanol | 699.08 g |

The reactor was sealed and purged with an inert gas. The following heating profile was initiated:

| | |
|---|---|
| Heat to 125° C. | 4 hours |
| Hold at 125° C. | 12 hours |
| Cool to 35° C. | 1 hour |

After the heating profile was complete, the polymer solution was discharged from the reactor. The resultant material was a viscous clear yellow solution. This material, when laid down as a film and allowed to dry, resulted in a very flexible film. This same material can be exchanged with water to give a water-based polymer solution having similar properties to the ethanol-based material.

Step 2

This step was carried out as in Example 1 to provide similar results.

The compositions herein are particularly useful in products for personal care, including, but not limited to, gels, lotions, mousses, sprays, fixatives, shampoos, conditioners, 2-1 shampoos, temporary hair dyes, semi-permanent hair dyes, permanent hair dyes, straighteners, permanent waves, relaxers, creams, putties, waxes and pomades. The compositions can be used alone or in combination with anionic, nonionic and cationic hair styling polymers, thickeners, film formers, surfactants, reducing agents, oxidizers and other ingredients typically found in personal care products. Specific examples follow:

Gels:

Hair and/or skin care compositions wherein the compositions comprise an aqueous or hydroalcoholic gel. Gels can be in the form of spray gels, fluid gels, tube gels and thick viscous tub gels. The compositions are preferably employed at use levels of 0.1–10% by weight in anionic, nonionic or cationic gellants, or combinations thereof, such gallants preferably being present in amounts of 0.1–5% by weight.

Anionic gellants include, but are not limited to, Carbomer®, acrylates/C10–30 alkyl acrylate crosspolymer, acrylates copolymer, acrylates/beheneth-25 methacrylate copolymer, acylates/steareth-20 methacrylate copolymer, polyvinylmethyl ether/maleic anhydride PVM/MA, alkyldiene, e.g. decadiene or octadiene crosspolymer, xanthan gum, sodium polyacrylate, polyacrylamide, copolymers of sodium acrylates, and copolymers of polyacrylamide.

Nonionic gellants include, but are not limited to, guar and their derivatives, and celluloses and their derivatives. Examples are hydroxyethyl cellulose, hydroxypropyl cellulose, hydroxymethyl cellulose, hydroxypropylmethyl cellulose and hydroxypropyl guar.

Cationic thickeners include, but are not limited to, Polyquaternium 32 (and) mineral oil, and Polyquaternium 37 (and) mineral oil (and) PPG-1 Trideceth-6.

Hair and skin care gel formulations with the compositions herein using crosslinked homopolymers of acrylic acid, e.g., Carbomer® and/or acrylates/C10–30 alkyl acrylate crosspolymer as the gellant result in synergistic performance in moisture resistance. In particular, hair styling gels with the above listed combinations show synergistic high humidity resistance on hair.

The complexation of the compositions with Carbomer® and/or acrylates/C10–30 alkyl acrylate crosspolymer results in clear films upon draw down. The resultant viscosity, yield value and suspension capabilities are unaffected or increased by the addition of such compositions into the gellant.

FORMULATION EXAMPLES (% by wt)

Hair Styling Gel Formulation 1
  Water—QS to 100%
  Carbomer®—0.5
  Triethanolamine (99%)—0.5
  Isobutylene/dimethylaminopropylmaleimide/ethoxylated Maleimide/maleic acid copolymer (30%)—6.66
  Benzophenone-4—0.05
  Disodium EDTA—0.10
  Triethanolamine (99%)—adjust to pH 7
  Propylene glycol (and) diazolidinyl urea (and) iodopropynyl butylcarbamate—0.5

Hair Styling Gel Formulation 2
  Water—QS to 100%
  Isoceteth-20—0.5
  Isobutylene/dimethylaminopropylmaleimide/ethoxylated Maleimide/maleic acid copolymer (30%)—6.66
  Aminomethyl propanol—0.25
  Acrylates/beheneth-25 methacrylate copolymer (20%)—4.7
  Propylene glycol (and) diazolidinyl urea (and) iodopropynyl butylcarbamate—0.5

Hair Styling Cream
  Water—QS to 100%
  Sodium polyacrylate (and) hydrogenated polydecene (and) trideceth-6—2.0
  Isobutylene/dimethylaminopropylmaleimide/ethoxylated maleimide/maleic acid copolymer (30%)—6.7
  Glycerin—2.0
  Cetyl PEG/PPG-15/15 butyl ether dimethicone—1.0
  Propylene glycol (and) diazolidinyl urea (and) iodopropynyl butylcarbamate—0.5

Mousses:

The compositions are incorporated into aerosol and non-aerosol hair and skin mousse formulations, as well as spray mousses which utilize an aerosol valve with a dip tube and a mechanical break-up actuator to deliver an atomized spray foam. They are also compatible in aerosol and non-aerosol shave foam applications. Preferred use levels of the active polymer mixture are 0.1–10.0% by weight.

Shampoos and Body Washes:

The compositions are compatible with anionic, amphoteric, cationic and nonionic surfactants. The compositions are incorporated into cleansing formulations for hair and body. The compositions are used at polymer use levels of 0.1 to 10% by weight with anionic, amphoteric, cationic, and nonionic surfactants, or combinations thereof, such surfactants preferably being present in amounts of 0.1 to 20% by weight.

Clear Shampoo Formulation:
  Water—QS to 100%
  Isobutylene/dimethylaminopropylmaleimide/ethoxylated maleimide/maleic acid copolymer—5.0
  Cocamidopropyl betaine (34.5%)—10.00
  Cocoamphodiacetate (50%)—5.00
  Sodium laureth sulfate (25.6)—17.5
  Ammonium lauryl sulfate (29.2%)—17.5
  Propylene glycol (and) diazolidinyl urea (and) iodopropynyl butylcarbamate—0.30
  Citric Acid—0.25

Oil-in-Water Emulsions and Hair Conditioners:

The compositions are incorporated in hair and skin oil-in-water emulsions. In hair conditioners, the polymer mixtures are compatible with quaternary ammonium compounds. The use level of surfactants/emulsifiers suitably is from 0.1 to 10% by weight.

Conditioner Formulation:
  Phase A:
  Water—QS to 100%
  Citric Acid—0.25
  Hydroxyethyl cellulose—0.5
  Disodium EDTA—0.1
  Phase B:
  Cetearyl Alcohol—4.0
  Steareth-10—1.0
  Glyceryl stearate (and) PEG-100 stearate—2.5
  Dicetyldimonium chloride (68.2%)—2.0
  Phase C:
  Isobutylene/dimethylaminopropylmaleimide/ethoxylated maleimide/maleic acid copolymer (30%)—6.6
  Propylene glycol (and) diazolidinyl urea (and) iodopropynyl butylcarbamate—0.5
  Wheat amino acid—0.5

Process:

Heat Phases A and B separately to 75° C. Add Phase B to Phase A with agitation. Mix until uniform and cool to 45° C. Continue mixing and add ingredients in Phase C one at a time with mixing until homogenous.

Oxidative Hair Dyes:

The polymers are incorporated into oxidative hair dye formulations including semi-permanent and permanent hair dye products, suitably at use levels of 0.1–10% by weight.

Formulation:
  Water—QS to 100%
  Oleic acid—5
  C11–15 pareth-9—3
  Isobutylene/dimethylaminopropylmaleimide/ethoxylated maleimide/maleic acid copolymer (30%)—3.0
  Ammonium hydroxide—2
  Steareth-21—2
  Propylene glycol—2
  Cetyl alcohol—2
  PEG150/Stearyl/SMDI copolymer—3
  Stearyl alcohol—1
  Sodium sulfite—1
  Iron oxides—0.5
  Mica—0.2
  1-Naphitol—0.2
  p-Phenylenediamine—0.2
  Titanium dioxide—0.1

Relaxers and Permanent Waves:

The compositions are used as relaxer and permanent wave formulations, suitably in amounts of 0.1%–10% by weight. They may be combined with hair reducing agents, including, but not limited to, ammonium thioglycolate, guanidine hydroxide, sodium bisulfite and the like.

Formulation:
  Crème Hair Relaxer Base: To be mixed with guanidine carbonate
  Activator Solution
  Water—QS to 100%
  Petrolatum—10
  Paraffin Wax—8
  Mineral oil—6
  Isobutylene/dimethylaminopropylmaleimide/ethoxylated maleimide/maleic acid copolymer (30%)—5.0
  Cetearyl alcohol—3
  Calcium hydroxide—3
  Polysorbate 80—2
  Laneth-15—2
  PEG-75 lanolin oil—1
  Cocamphodipropionate—1

Hair Sprays:

The compositions are formulated as hair sprays, both non-aerosol and aerosol, suitably at use levels of 0.1–10% by weight. Aerosol hair sprays can include up to 60% hydrocarbon, 70% dimethyl ether, 50% hydrofluorocarbon 152a, or combinations thereof. Hair spray formulations include, but are not limited to, alcohol-free pump hair sprays, 55%–95% VOC pump and aerosol hair sprays.

Formulation:
  Clear Alcohol Free Pump Hair Spray
  Water—QS to 100%
  Sodium lauryl sulfate (25%)—0.25
  Isobutylene/dimethylaminopropylmaleimide/ethoxylated maleimide/maleic acid copolymer (30%)—13.33
  Propylene glycol (and) diazolidinyl urea (and) iodopropynyl butylcarbamate—0.5
  Pump—Calmar Marks® VI WL-31

Personal Care Applications:

The compositions are blended with anionic, nonionic and cationic hair styling polymers, thickeners, and film formers; and with anionic, nonionic and cationic surfactants. Clarity in water is increased with low levels of charged surfactants (0.1–2% by weight).

The compositions also are formulated into bodifying leave-on and rinse-off hair preparations. They also can be formulated into flexible hold styling products which provide smooth, continuous films on hair that have strength and will bend under both high and low stress.

Skin Care Applications:

The compositions are used as a film former (a) for the enhancement of antiperspirants to either increase overall wetness protection or to effect a reduction in the amount of conventional actives therein while holding equivalent efficacy; (b) to increase the substantivity of a deodorant active for better and longer acting deodorancy; (c) in an anti-bacterial liquid hand soap to increase efficacy and for longer lasting claim; (d) for holding products on skin; (e) to increase contact time of a therapeutic skin product containing an active, including, but not limited to, Betulin, Vitamins E, A and C, ceramides, allantoin, lycopenes, bisabolol, retinol, and the like, and (f) to aid in the removal of sebum, and/or villous hair.

The compositions also are used in make-up products, e.g. foundation, mascara, bronzers, eyeliners, to effect film formation, wear resistance and pigment dispersion. They are also used in mascaras for curl retention.

While the invention has been described with particular reference to certain embodiments thereof, it will be understood that changes and modifications may be made which are within the skill of the art.

What is claimed is:

1. A personal care composition which includes a mixture of (A), a polymer characterized structurally by repeat units of (a) a monomer-maleic anhydride alkyl half-ester or full acid, (b) maleamic acid, and (c) maleimide, of the formulas:

(a) half-ester or full acid

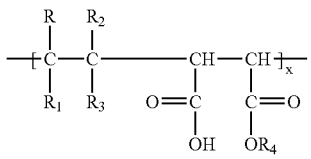

(b) maleamic acid

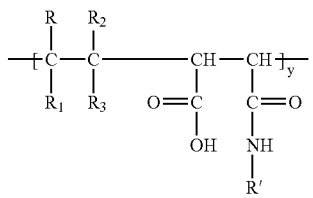

(c) maleimide

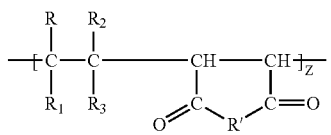

where:
R, $R_1$, $R_2$ and $R_3$ are selected from H, alkyl, alkoxy, cycloalkyl, aryl, ester, acid, hydroxy, hydroxyalkyl, amido, amino, lactam, chloro, fluoro, halo and silyl, and $R_4$ is H or alkyl; and
R' is a derivatizing group which is a polyoxyalkylene amine, having the formula:

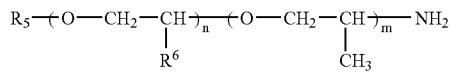

where $R_5$ and $R_6$ are selected from H and alkyl; and n and m are integers from 1–50;
x, y and z are present, in mole %, of 0–99.9, 0–50 and 0.1–100, respectively;
and (B) a compound or polymer having a carboxylic acid functionality water and/or ethanol.

2. A personal care composition according to claim 1 wherein x=0–50, y=0–5 and z=5–100.

3. A personal care composition according to claim 1 wherein said derivatizing group also includes 3-(dimethylamino) propylamine.

4. A personal care composition according to claim 3 wherein wherein said 3-(dimethylamino) propyl amine and said polyoxyalkylene amine are present in a mole ratio of 40:98:1–10.

5. A personal care composition according to claim 4 wherein $R_5$ is $CH_3$ and $R_6$ is H.

6. A personal care composition according to claim 4 wherein both $R_5$ and $R_6$ are $CH_3$.

7. A personal care composition according to claim 4 wherein n=32 and m=10.

8. A personal care composition according to claim 1 wherein, in (a), said monomer is an α-olefin.

9. A personal care composition according to claim 1 wherein (B) is a crosslinked carboxylic acid containing polymer.

10. A personal care composition according to claim 9 wherein (B) is a crosslinked acrylic acid polymer.

11. A personal care composition according to claim 1 wherein (B) is a linear carboxylic acid containing polymer.

12. A personal care composition according to claim 1 wherein (B) is an acrylic acid containing polymer.

13. A personal care composition according to claim 1 wherein (A) and (B) are present and the mole ratio of maleimide in (A) to the carboxylic units in (B) is about 1:1.

14. A personal care composition according to claim 1 which is a hair care composition exhibiting excellent high humidity curl retention.

15. A hair care composition according to claim 14 which is a styling, mousse, gel or spray formulation.

16. A cosmetic film-forming composition according to claim 1 for producing a water-resistant film demonstrating excellent hold, and durability properties.

17. A cosmetic film-forming composition according to claim 16 which is a mascara product exhibiting excellent high humidity and moisture resistance.

* * * * *